United States Patent

Nagamine et al.

Patent Number: 5,500,424
Date of Patent: Mar. 19, 1996

[54] PYRIMIDINE AND PYRIDINE DERIVATIVES, THEIR PRODUCTION AND USE

[75] Inventors: Masashi Nagamine, Gose; Kenji Yamamoto, Kawachinagano; Kenji Horiuchi, Daito; Yoshimitsu Matsui, Kawachinagano; Masanori Yoshida, Hashimoto, all of Japan

[73] Assignee: Nihon Nohyaku Co., Ltd., Tokyo, Japan

[21] Appl. No.: 288,699

[22] Filed: Aug. 12, 1994

[30] Foreign Application Priority Data

Aug. 13, 1993 [JP] Japan ................... 5-222085

[51] Int. Cl.$^6$ ............. A61K 31/535; A61K 31/54; A61K 31/495; A61K 31/505; A61K 31/44; C07D 417/00; C07D 413/00; C07D 403/00; C07D 213/02; C07D 401/00; C07D 211/72

[52] U.S. Cl. ............. 514/235.5; 514/227.8; 514/235.8; 514/252; 514/269; 514/273; 514/274; 514/318; 514/332; 514/343; 514/349; 544/60; 544/121; 544/122; 544/129; 544/130; 544/295; 544/316; 544/322; 544/357; 544/360; 544/372; 546/194; 546/281; 546/290; 546/306; 546/309

[58] Field of Search ............. 544/121, 322, 544/357, 360, 372, 60, 122, 129, 130, 295, 316, 360; 546/306, 194, 281, 290, 309; 514/252, 349, 227.8, 235.5, 235.8, 269, 273, 274, 318, 332, 342

[56] References Cited

U.S. PATENT DOCUMENTS

| | | | |
|---|---|---|---|
| 4,716,175 | 12/1987 | Hoefle et al. | 514/357 |
| 4,722,927 | 2/1988 | Holmes | 514/256 |
| 4,994,465 | 2/1991 | Trivedi | 514/256 |
| 5,185,358 | 2/1993 | Creswell et al. | 514/383 |

FOREIGN PATENT DOCUMENTS

| | | |
|---|---|---|
| 0354994 | 2/1990 | European Pat. Off. . |
| 0370740 | 5/1990 | European Pat. Off. . |
| 0421456 | 5/1991 | European Pat. Off. . |
| 0477778 | 4/1992 | European Pat. Off. . |
| 0540854 | 5/1993 | European Pat. Off. . |
| 0613894 | 9/1994 | European Pat. Off. . |
| 92-19614 | 11/1992 | WIPO . |
| 93-24458 | 12/1993 | WIPO . |

Primary Examiner—Cecilia Tsang
Attorney, Agent, or Firm—Cushman Darby & Cushman

[57] ABSTRACT

The present invention relates to a compound represented by the general formula (I):

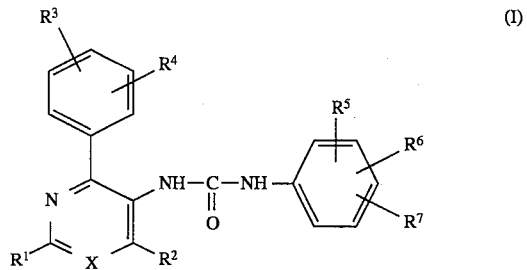

[wherein $R^1$ is a lower alkyl group or the like, $R^2$ is a lower alkyl group or the like, $R^3$ and $R^4$, which may be the same or different, are halogen atoms or the like, $R^5$, $R^6$ and $R^7$, which may be the same or different, are halogen atoms or the like, and X is =N— or =CH—] or a pharmacologically acceptable salt thereof, which has inhibitory effect on acyl-CoA:cholesterol O-acyltransferase (ACAT), a process for producing said compound, and uses of said compound.

6 Claims, No Drawings

PYRIMIDINE AND PYRIDINE DERIVATIVES, THEIR PRODUCTION AND USE

BACKGROUND OF THE INVENTION

1. Field of the Invention

The present invention relates to pyrimidine and pyridine derivatives or pharmacologically acceptable salts thereof, which have an excellent inhibitory effect on acyl-CoA:cholesterol O-acyltransferase (ACAT).

The compounds of the present invention have the effect of reducing serum cholesterol by inhibiting the absorption of cholesterol from intestinal tract and suppress the accumulation of cholesterol esters in the arterial wall. Therefore, they are useful as a prophylactic and therapeutic agent for hypercholesterolemia, atherosclerosis and various diseases caused by them (for example, ischemic heart diseases such as myocardial infarction, and cerebrovascular diseases such as cerebral infarction and cerebral apoplexy).

2. Related Art

Japanese Patent Unexamined Publication Nos. 61-40272 and 1-207234 disclose compounds (e.g. 5-[3-(2-dimethylaminoethyl)ureido]- 6-methyl-4-(3-nitrophenyl)-2-phenylpyrimidine) and 3-[3-(2-dimethylaminoethyl)ureido]-4-(3-nitrophenyl)-2-methyl-6-phenylpyridine, respectively, as pharmaceutical compositions for curing cerebrovascular diseases. Japanese Patent Unexamined Publication No. 5-320028 discloses compounds such as 4-(phenylureido)pyridine and 4-(phenylureido)pyrimidine as hair tonics. But, these references do not describe the above compounds as having ACAT-inhibitory activity or serum-cholesterol-lowering activity, at all. Japanese Patent Unexamined Publication Nos. 62-258366, 63-253060, 2-258756 and 5-92950 disclose pyrimidine and pyridine derivatives having ACAT-inhibitory effect, but the effect of all the pyrimidine and pyridine derivatives are not sufficient.

SUMMARY OF THE INVENTION

The present invention provides novel pyrimidine and pyridine derivatives or pharmacologically acceptable salts thereof, a process for production of the derivatives, and ACAT inhibitors containing the derivative or the salt as an active ingredient.

DETAILED DESCRIPTION OF THE INVENTION

The present inventors found that novel compounds not known in any literature, N-phenyl-N'-(4-phenylpyrimidin-5-yl)urea and N-phenyl-N'-(4-phenyl-pyridin- 5-yl)urea derivatives represented by the general formula (I):

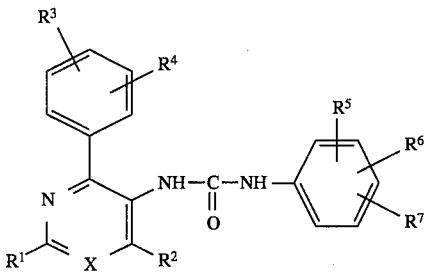

[wherein $R^1$ is a lower alkyl group, a lower cycloalkyl group, a lower alkoxy group, an aliphatic cyclic amino group which may be substituted by one or more lower alkyl groups, or a phenyl group which may be substituted by one or more halogen atoms, $R^2$ is a hydrogen atom or a lower alkyl group, $R^3$ and $R^4$, which may be the same or different, are hydrogen atoms, halogen atoms, lower alkyl groups, lower haloalkyl groups, lower alkoxy groups or lower alkylthio groups, $R^5$, $R^6$ and $R^7$, which may be the same or different, are hydrogen atoms, halogen atoms, lower alkyl groups, lower haloalkyl groups, lower alkoxy groups, lower alkylthio groups or lower dialkylamino groups, and X is =N— or =CH—] have ACAT-inhibitory activity much higher than that of well-known pyrimidine and pyridine derivatives and are useful as a serum cholesterol lowering agent or an agent for curing arteriosclerosis, whereby the present invention has been accomplished.

In the above general formula (I), the halogen atoms include fluorine atom, chlorine atom, bromine atom and iodine atom. The lower alkyl groups include linear or branched alkyl groups having 1 to 8 carbon atoms, such as methyl, ethyl, n-propyl, isopropyl, n-butyl, isobutyl, sec-butyl, tert-butyl, n-pentyl, isopentyl, neopentyl, 1-methylbutyl, 2-methylbutyl, 1,2-dimethylpropyl, n-hexyl, isohexyl, 1-methylpentyl, 2-methylpentyl, 3-methylpentyl, 1,1-dimethylbutyl, 1,2-dimethylbutyl, 2,2-dimethylbutyl, 1,3-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl, 1-ethyl-2-methylpropyl and the like. The lower cycloalkyl group includes cyclopropyl group, cyclobutyl group, cyclopentyl group, cyclohexyl group, cycloheptyl group, etc. The lower haloalkyl groups include trichloromethyl group, trifluoromethyl group, 1,1,1-trifluoroethyl group, etc. The lower alkoxy groups include methoxy group, ethoxy group, n-propoxy group, isopropoxy group, n-butoxy group, isobutoxy group, sec-butoxy group, tertbutoxy group, etc. The lower alkylthio groups include methylthio group, ethylthio group, n-propylthio group, isopropylthio group, n-butylthio group, isobutylthio group, sec-butylthio group, tert-butylthio group, etc. The aliphatic cyclic amino group which may be substituted by one or more lower alkyl groups includes pyrrolidino group, piperidino group, morpholino group, 2-methylmorpholino group, 2,6-dimethylmorpholino group, thiomorpholino group, piperazino group, N-methylpiperazino group, etc. The lower dialkylamino groups include dimethylamino group, diethylamino group, di-n-propylamino group, diisopropylamino group, di-nbutylamino group, etc.

Preferable examples of the compounds of the present invention are N-[4-(2-chlorophenyl)-6-methyl-2-phenylpyrimidin- 5-yl]-N'-(2,6-diisopropylphenyl)urea, N-( 2,6-diisopropylphenyl)-N'-[4-(2-fluorophenyl)-2-phenylpyrimidin- 5-yl]urea, N-(2,6-diisopropylphenyl)-N'-[4-(2-methoxyphenyl)- 2-phenylpyrimidin-5-yl]urea, N-[4-(2-chlorophenyl)- 2-isopropylpyrimidin-5-yl]-N'-(2,6-diethylphenyl)urea, N-[2-t-butyl-4-(2-chlorophenyl)pyrimidin- 5-yl]-N'-(2,6-diisopropylphenyl)urea, N-[4-(2-chlorophenyl)-2-ethoxypyrimidin-5-yl]-N'-(2,6-diisopropylphenyl)urea, N-[4-(2-chlorophenyl)-2-(N-pyrrolidino)pyrimidin- 5-yl]-N'-(2,6-diethylphenyl)urea, N-[4-(2-chlorophenyl)-2-(N-piperidino)pyrimidin-5-yl]-N'-( 2,6-diisopropylphenyl)urea, N-[2-(2-chlorophenyl-6-phenylpyridin- 3-yl]-N'-(2,6-diethylphenyl)urea, and N-[ 2-(2-chlorophenyl)-6-cyclohexylpyridin-3-yl]-N'-(2,6-diethylphenyl)urea.

Particularly preferable examples of the compounds of the present invention are N-[4-(2-chlorophenyl)- 2-phenylpyrimidin-5-yl]-N'-(2,6-diethylphenyl)urea, N-[4-(2-chlorophenyl)-2-phenylpyrimidin-5-yl]-N'-( 2,6-diisopropylphenyl)urea, N-(2,6-diisopropylphenyl)-N'-[ 2,4- diphenylpyrimidin-5-yl]urea, N-(2,6-diisopropylphenyl)-N'-[ 4-(2-methylphenyl)-2-phenylpyrimidin- 5-yl]urea, N-(2,6-diethylphenyl)-N'-[2-phenyl- 4-(2-trifluoromethylphenyl)pyrimidin-5-yl]urea, N-(2,6-diethylphenyl)-N'-[ 4-(2-methylthiophenyl)-2-phenylpyrimidin- 5-yl]urea, N-[4-(2-chlorophenyl)-2-(N-piperidino)pyrimidin- 5-yl]-N'-(2,6-diethylphenyl)urea, N-[4-(2-chlorophenyl)-2-(N-morpholino)pyrimidin-5-yl]-N'-( 2,6-diethylphenyl)urea, N-[2-(2-chlorophenyl)-6-methylpyridin- 3-yl]-N'-(2,6-diisopropylphenyl)urea, and N-[2-(2-chlorophenyl)-6-cyclohexylpyridin-3-yl]-N'-(2,6-diisopropylphenyl)urea.

The compound of the general formula (I) can be synthesized by a process represented by the following formulas:

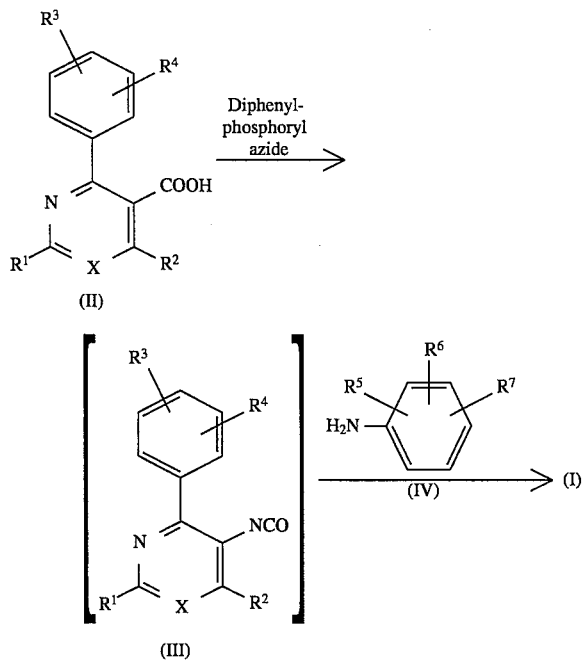

wherein $R^1$, $R^2$, $R^3$, $R^4$, $R^5$, $R^6$, $R^7$ and X are as defined above.

In detail, the compound of the general formula (I) can be produced by reacting a compound of the general formula (II) with diphenylphosphoryl azide in the presence of an organic amine such as triethylamine in an inert solvent such as benzene, toluene, xylene, fluorobenzene or dioxane in a temperature range of room temperature to about 150° C. to obtain an isocyanate (III), and then reacting the isocyanate with a compound of the general formula (IV) in a temperature range of room temperature to about 150° C. without isolating the isocyanate. Since the reactions are equimolar reactions, it is sufficient that the reactants for carrying out each reaction are used in equimolar amounts, though either of them may be used in excess.

The compound of the general formula (II) used in the reaction can be synthesized by any of the following processes.

Process A

A compound of the general formula (II) in which X is =N— and $R^2$ is a hydrogen atom can be synthesized from a compound of the general formula (V) by the process described in Journal of Heterocyclic Chemistry p. 183 (1981) or a process based thereon.

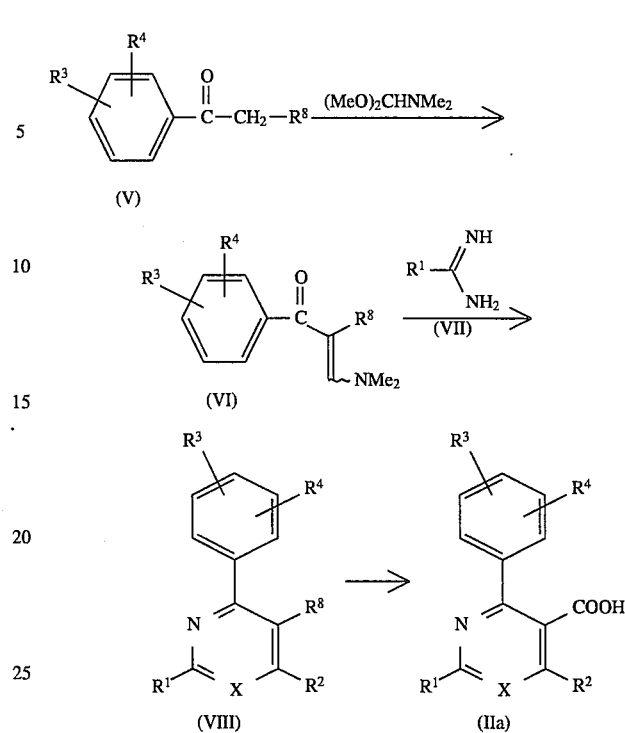

wherein $R^1$, $R^3$ and $R^4$ are as defined above, $R^8$ is $COOR^9$ (wherein $R^9$ is a $C_1$–$C_4$ alkyl group) or a nitrile group, and Me is a methyl group.

In detail, a compound (V) can be converted into a compound (VI) by its reaction with a dimethylformamide dialkylacetal in an inert solvent (e.g. benzene, toluene or xylene) or without a solvent in a temperature range of room temperature to about 150° C. Then, the compound (VI) can be converted into a pyrimidine (VIII) by its reaction with an amidine (VII) in an ordinary solvent (e.g. methanol, ethanol, isopropanol or dioxane) in a temperature range of room temperature to about 100° C. Subsequently, the pyrimidine (VIII) is hydrolyzed with an aqueous alkali solution (e.g. sodium hydroxide or potassium hydroxide) or a mineral acid (e.g. hydrochloric acid, sulfuric acid or hydrobromic acid), whereby a carboxylic acid (IIa) can be produced. As a solvent used in this reaction, methanol, ethanol, isopropanol, dioxane, etc. are suitable. The reaction may be carried out without a solvent. The reaction temperature is preferably in a range of room temperature to about 120° C.

Process B

A compound of the general formula (II) in which X is =N— and $R^2$ is a lower alkyl group can be synthesized from a compound of the general formula (IX) by the process described in Chem. Phar. Bul. 40, 2423 (1992) or a process based thereon.

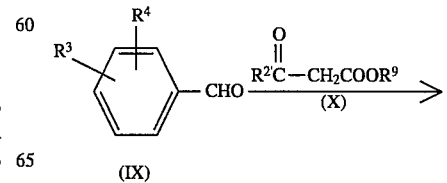

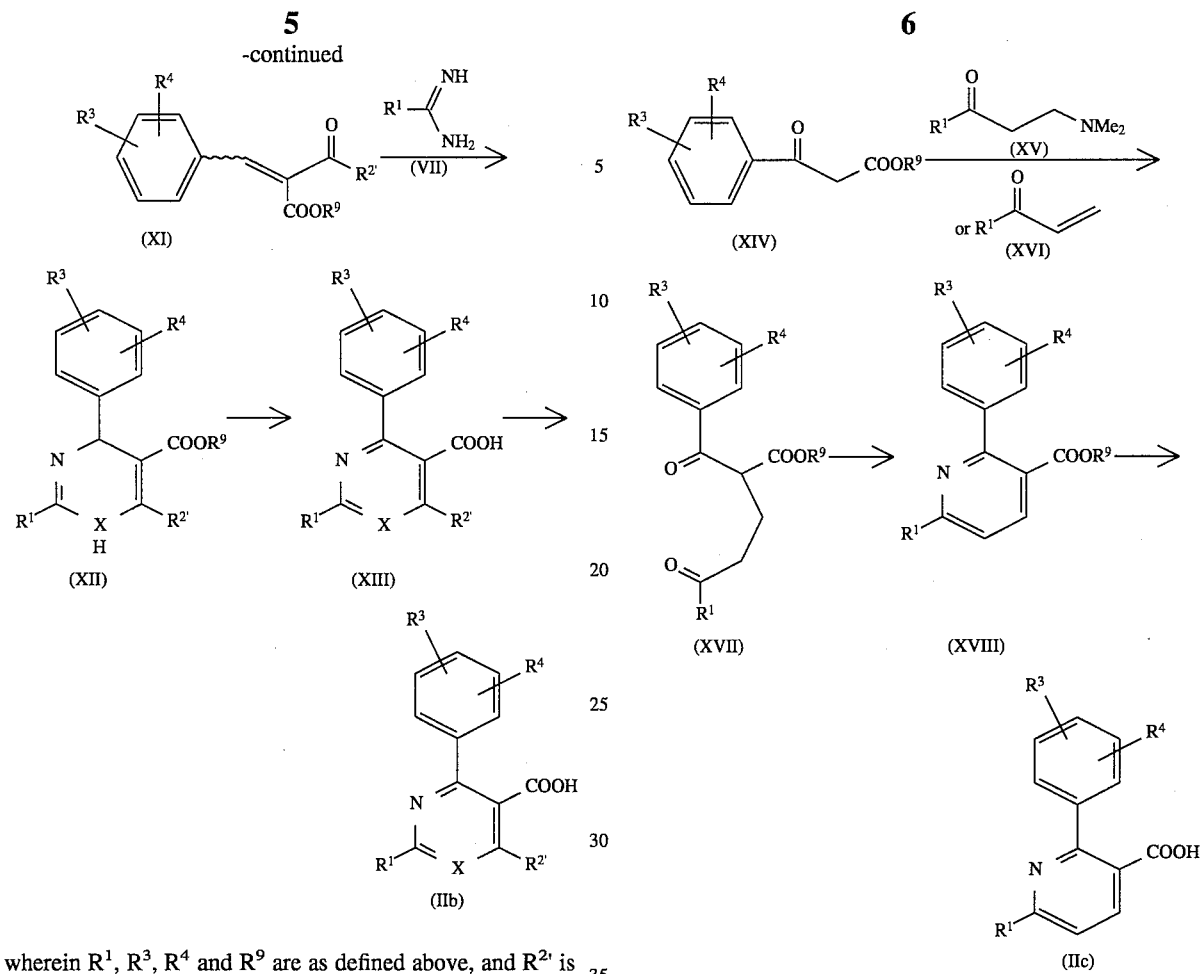

wherein $R^1$, $R^3$, $R^4$ and $R^9$ are as defined above, and $R^{2'}$ is a lower alkyl group.

In detail, a benzaldehyde (IX) can be converted into a compound (XI) by its reaction with a β-keto-ester (X) in the presence of an organic base (e.g. triethylamine, pyridine, piperazine or piperidine) and an organic acid (e.g. acetic acid). This reaction is carried out preferably in an inert solvent (e.g. benzene, toluene or xylene) in a temperature range of room temperature to about 150° C. Then, the compound (XI) can be converted into a dihydropyrimidine (XII) by its reaction with an amidine (VII) in an ordinary solvent (e.g. methanol, ethanol, isopropanol, n-butanol or dioxane) in a temperature range of room temperature to about 100° C. Subsequently, the oxidation of the dihydropyridine (XII) into a pyrimidine (XIII) can be carried out with an oxidizing agent such as manganese dioxide, nickel peroxide, sulfur, 2,3-dichloro-5,6-dicyano-1,4-benzoquinone, potassium permanganate, or palladium-carbon. Thereafter, the pyrimidine (XIII) can be converted into a carboxylic acid (IIb) in the same manner as in process A.

Process C

A compound of the general formula (II) in which X is =C— and $R^2$ is a hydrogen atom can be synthesized from a compound of the general formula (XIV) by a process represented by the following formulas.

wherein $R^1$, $R^3$, $R^4$, and $R^9$ and Me are as defined above.

In detail, a β-keto-ester (XIV) can be converted into a compound (XVII) by its reaction with a Mannich base (XV) or a vinylketone (XVI) in the presence of a metal alkoxide (e.g. sodium methoxide, sodium ethoxide or potassium t-butoxide) or a metal hydride (e.g. sodium hydride or potassium hydride). This reaction is carried out preferably in an ordinary solvent (e.g. methanol, ethanol, isopropanol, t-butanol, tetrahydrofuran, ether or dioxane) in a temperature range of room temperature to about 100° C. Then, the compound (XVII) can be converted into a nicotinic ester (XVIII) by its reaction with a fatty acid ammonium (e.g. ammonium formate or ammonium acetate) in the presence of ferric chloride. This reaction is carried out preferably in a solvent such as formic acid or acetic acid in a temperature range of room temperature to about 120° C. Thereafter, the nicotinic ester (XVIII) can be converted into a carboxylic acid (IIC) in the same manner as in process A.

Typical examples of compounds of the general formula (I) obtained by the above production processes are given in Table 1, but they are not intended in any way to limit the scope of the present invention.

In the Table, the following abbreviations are used to stand for the substituent groups as specified below:

Ph; phenyl,
Me; methyl,
Et; ethyl,
iPr; isopropyl,
tBu; tert-butyl, and
nHep; n-heptyl.

TABLE 1

[Structure: central urea linkage, left side is a pyrimidine/pyridine ring with R¹, R², X, bearing a phenyl group with R³, R⁴; right side phenyl with R⁵, R⁶, R⁷]

| Compound No. | X | R¹ | R² | R³ | R⁴ | R⁵ | R⁶ | R⁷ |
|---|---|---|---|---|---|---|---|---|
| 1 | N | Ph | Me | 2-Cl | H | 2-iPr | 6-Me | H |
| 2 | N | Ph | Me | 2-Cl | H | 2-iPr | 6-iPr | H |
| 3 | N | Ph | Me | 2-Cl | H | 2-Me | 4-Me | 6-Me |
| 4 | N | Ph | Me | 2-Cl | H | 2-F | 4-F | H |
| 5 | N | Ph | Me | 2-Cl | H | 2-F | 4-F | 6-F |
| 6 | N | Ph | Me | 2-Cl | H | 4-NMe$_2$ | H | H |
| 7 | N | Ph | H | 2-Cl | H | H | H | H |
| 8 | N | Ph | H | 2-Cl | H | 2-CF$_3$ | H | H |
| 9 | N | Ph | H | 2-Cl | H | 2-OMe | H | H |
| 10 | N | Ph | H | 2-Cl | H | 2-SMe | H | H |
| 11 | N | Ph | H | 2-Cl | H | 2-Me | 4-Me | H |
| 12 | N | Ph | H | 2-Cl | H | 3-Me | 4-Me | H |
| 13 | N | Ph | H | 2-Cl | H | 2-Me | 6-Me | H |
| 14 | N | Ph | H | 2-Cl | H | 2-Et | 6-Et | H |
| 15 | N | Ph | H | 2-Cl | H | 2-iPr | 6-iPr | H |
| 16 | N | Ph | H | 2-Cl | H | 2-iPr | 6-Me | H |
| 17 | N | Ph | H | 2-Cl | H | 2-tBu | 6-Me | H |
| 18 | N | Ph | H | 2-Cl | H | 2-Me | 4-Me | 6-Me |
| 19 | N | Ph | H | 2-Cl | H | 2-NMe$_2$ | 6-Me | H |
| 20 | N | Ph | H | 2-Cl | H | 2-F | 4-Me | H |
| 21 | N | Ph | H | 2-Cl | H | 2-F | 4-F | H |
| 22 | N | Ph | Me | 2-Cl | H | 2-F | 6-F | H |
| 23 | N | Ph | Me | 2-Cl | H | 2-F | 4-F | 6-F |
| 24 | N | Ph | Me | 2-Cl | H | 2-Br | 6-Br | H |
| 25 | N | Ph | Me | 3-Cl | H | 2-Et | 6-Et | H |
| 26 | N | Ph | Me | 3-Cl | H | 2-iPr | 6-iPr | H |
| 27 | N | Ph | Me | 4-Cl | H | 2-Et | 6-Et | H |
| 28 | N | Ph | H | 4-Cl | H | 2-iPr | 6-iPr | H |
| 29 | N | Ph | H | 2-Cl | 4-Cl | 2-Et | 6-Et | H |
| 30 | N | Ph | H | 2-Cl | 4-Cl | 2-iPr | 6-iPr | H |
| 31 | N | Ph | H | H | H | 2-Et | 6-Et | H |
| 32 | N | Ph | H | H | H | 2-iPr | 6-iPr | H |
| 33 | N | Ph | H | 2-F | H | 2-Et | 6-Et | H |
| 34 | N | Ph | H | 2-F | H | 2-iPr | 6-iPr | H |
| 35 | N | Ph | H | 2-Me | H | 2-Et | 6-Et | H |
| 36 | N | Ph | H | 2-Me | H | 2-iPr | 6-iPr | H |
| 37 | N | Ph | H | 2-CF$_3$ | H | 2-Et | 6-Et | H |
| 38 | N | Ph | H | 2-CF$_3$ | H | 2-iPr | 6-iPr | H |
| 39 | N | Ph | H | 2-OMe | H | 2-Et | 6-Et | H |
| 40 | N | Ph | H | 2-OMe | H | 2-iPr | 6-iPr | H |
| 41 | N | Ph | H | 2-SMe | H | 2-Et | 6-Et | H |
| 42 | N | Ph | H | 2-SMe | H | 2-iPr | 6-iPr | H |
| 43 | N | 2,5-dichlorophenyl | H | 2-Cl | H | 2-Et | 6-Et | H |
| 44 | N | 2,5-dichlorophenyl | H | 2-Cl | H | 2-iPr | 6-iPr | H |
| 45 | N | Me | H | 2-Cl | H | 2-Et | 6-Et | H |
| 46 | N | Me | H | 2-Cl | H | 2-iPr | 6-iPr | H |
| 47 | N | iPr | H | 2-Cl | H | 2-Et | 6-Et | H |

TABLE 1-continued

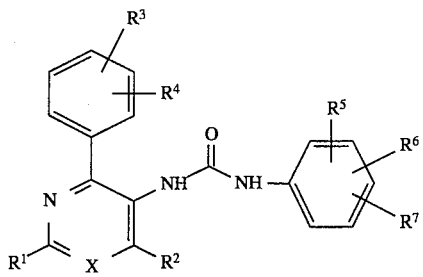

| Compound No. | X | R¹ | R² | R³ | R⁴ | R⁵ | R⁶ | R⁷ |
|---|---|---|---|---|---|---|---|---|
| 48 | N | iPr | H | 2-Cl | H | 2-iPr | 6-iPr | H |
| 49 | N | tBu | H | 2-Cl | H | 2-Et | 6-Et | H |
| 50 | N | tBu | H | 2-Cl | H | 2-iPr | 6-iPr | H |
| 51 | N | OEt | H | 2-Cl | H | 2-Et | 6-Et | H |
| 52 | N | OEt | H | 2-Cl | H | 2-iPr | 6-iPr | H |
| 53 | N | pyrrolidin-1-yl | H | 2-Cl | H | 2-Et | 6-Et | H |
| 54 | N | pyrrolidin-1-yl | H | 2-Cl | H | 2-iPr | 6-iPr | H |
| 55 | N | piperidin-1-yl | H | 2-Cl | H | 2-Et | 6-Et | H |
| 56 | N | piperidin-1-yl | H | 2-Cl | H | 2-iPr | 6-iPr | H |
| 57 | N | morpholin-4-yl | H | 2-Cl | H | 2-Et | 6-Et | H |
| 58 | N | morpholin-4-yl | H | 2-Cl | H | 2-iPr | 6-iPr | H |
| 59 | N | 4-methylpiperazin-1-yl | H | 2-Cl | H | 2-Et | 6-Et | H |
| 60 | N | 4-methylpiperazin-1-yl | H | 2-Cl | H | 2-iPr | 6-iPr | H |
| 61 | CH | Ph | H | H | H | 2-iPr | 6-iPr | H |
| 62 | CH | Ph | H | 2-Cl | H | 2-Et | 6-Et | H |
| 63 | CH | Ph | H | 2-Cl | H | 2-iPr | 6-iPr | H |
| 64 | CH | Me | H | 2-Cl | H | 2-iPr | 6-iPr | H |
| 65 | CH | nHep | H | 2-Cl | H | 2-iPr | 6-iPr | H |
| 66 | CH | cyclohexyl | H | 2-Cl | H | 2-Et | 6-Et | H |

TABLE 1-continued

| Compound No. | X | R¹ | R² | R³ | R⁴ | R⁵ | R⁶ | R⁷ |
|---|---|---|---|---|---|---|---|---|
| 67 | CH | cyclohexyl | H | 2-Cl | H | 2-iPr | 6-iPr | H |

The compounds of the present invention are administered as a prophylactic and therapeutic agent for hypercholesterolemia and atherosclerosis orally or parenterally (intramuscularly, subcutaneously or intravenously). They are administered to human beings preferably orally. Since the compounds of the present invention are applicable in themselves as ACAT inhibitors, they are contained in compositions as active ingredients usually in an amount of 0.01 to 100% by weight. Although the dose of the compounds is varied depending on the condition of a disease, age, sex, body weight, administration route, etc., the dose for an adult is usually 0.1 to 1000 mg per day.

When the compound of the present invention is formulated into a pharmaceutical form, it is prepared into powder, granules, tablets, dragees, capsules, pills, a suspension, solution, emulsion, ampule, injection, isotonic solution or the like by a conventional preparation method. When an oral solid pharmaceutical is prepared, an excipient and optionally a binder, wetting agent, disintegrator, surfactant, lubricant, dispersant, taste-improver, odor-improver, etc. are added to the active ingredient, and the resulting mixture is made into tablets, coated tablets, granules, capsules or the like by a conventional method. The excipient includes, for example, lactose, glucose, sorbitol, corn starch and mannitol. The binder includes, for example, poly(vinyl alcohol)s, poly(vinyl ether)s, ethyl cellulose, gum arabic, gelatin, hydroxypropyl cellulose and poly(vinylpyrrolidone)s. The disintegrator includes, for example, calcium carbonate, calcium citrate, dextrin, starch and gelatin powder. The lubricant includes, for example, magnesium stearate, talc and poly(ethylene glycol)s. The odor-improver includes, for example, cocoa powder, menthol, and peppermint oil. The tablets and the granules may be properly coated with a frosting, gelatin or the like if necessary. When an injection is prepared, a pH adjustor, buffer, surfactant, solubilizer, solvent, stabilizer, preservative, etc. are added to the active ingredient if necessary, and the resulting mixture is made into a subcutaneous, intramuscular or intravenous injection by a conventional method.

Examples, reference examples, formulation examples and test examples of the present invention are described below but should not be construed as limiting the scope of the invention.

EXAMPLE 1

N-[4-(2-Chlorophenyl)-6-methyl-2-phenylpyrimidin-5-yl]-N'-(2-isopropyl-6-methylphenyl)urea (compound 1)

To a stirred mixture of 325 mg of 4-(2-chlorophenyl)-6-methyl-2-phenyl-5-pyrimidinecarboxylic acid and 0.26 cc of diphenylphosphoryl azide in 5 cc of benzene was added dropwise 0.14 cc of triethylamine at room temperature. The resulting mixture was stirred at room temperature for 20 minutes and then heated under reflux for 20 minutes. After cooling, 0.18 cc of 2-isopropyl- 6-methylaniline was added, followed by refluxing for 2 hours. After cooling, water was added to the reaction mixture and extracted with chloroform. The extract was dried over magnesium sulfate, and distilled to remove the solvent. The crude product thus obtained was purified by a silica gel column chromatography (eluent: ethyl acetate-hexane) to obtain 350 mg of compound 1.

Yield 74.3%, m.p. 266°–267° C. NMR ($\delta$, ppm; DMSO-$d_6$) 1.07 (d, 2H), 2.03 (s, 3H), 2.60 (s, 3H), 2.99 (m, 1H), 6.98–7.13 (m, 3H), 7.42–7.66 (m, 7H), 7.71 (s, 1H), 8.02 (s, 1H), 8.29–8.40 (m, 2H).

The compounds described in Examples 2 to 6 were obtained in the same manner as in Example 1.

EXAMPLE 2

N-[4-(2-Chlorophenyl)-6-methyl-2-phenylpyrimidin-5-yl]-N'-(2,6-diisopropylphenyl)urea (compound 2)

Yield 69.1%, m.p. 233°–234° C.

EXAMPLE 3

N-[4-(2-Chlorophenyl)-6-methyl-2-phenylpyrimidin-5-yl]-N'-(2,4,6-trimethylphenyl)urea (compound 3)

Yield 75.3%, m.p. 250°–251° C.

EXAMPLE 4

N-[4-(2-Chlorophenyl)-6-methyl-2-phenylpyrimidin-5-yl]-N'-(2,4-difluorophenyl)urea (compound 4)

Yield 66.5%, m.p. 249°–250° C.

EXAMPLE 5

N-[4-(2-Chlorophenyl)-6-methyl-2-phenylpyrimidin-5-yl]-N'-(2,4,6-trifluorophenyl)urea (compound 5)

Yield 68.4%, m.p. 248°–249° C.

EXAMPLE 6

N-[4-(2-Chlorophenyl)-6-methyl-2-phenylpyrimidin-5-yl]-N'-(4-dimethylaminophenyl)urea (compound 6)

Yield 74.2%, m.p. 285°–285.5° C.

EXAMPLE 7

N-[4-(2-Chlorophenyl)-2-phenylpyrimidin-5-yl]-N'-phenylurea (compound 7)

To a stirred mixture of 311 mg of 4-(2-chlorophenyl)-2-phenyl-5-pyrimidinecarboxylic acid and 0.26 cc of diphenylphosphoryl azide in 5 cc of fluorobenzene was added dropwise 0.15 cc of triethylamine at room temperature. The resulting mixture was stirred at room temperature for 30 minutes and then heated at a temperature of 65°–70° C. for 10 minutes. After cooling, 0.11 cc of aniline was added and the resulting mixture was stirred heated at a temperature of 70° C. for 2 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform) to obtain 200 mg of compound 7.

Yield 49.9%, m.p. 195°–198° C. NMR (δ, ppm; DMSO-$d_6$) 7.00 (t, 1H), 7.29 (t, 2H), 7.41–7.43 (d, 2H), 7.50–7.51 (m, 3H), 7.60–7.64 (m, 3H), 7.71 (d, 1H), 7.93 (s, 1H), 8.31–8.34 (m, 2H), 9.16 (s, 1H), 9.56 (s, 1H).

The compounds described in Examples 8 to 44 were obtained in the same manner as in Example 7.

EXAMPLE 8

N-[4-(2-Chlorophenyl)-2-phenylpyrimidin-5-yl]-N'-(2-trifluoromethylphenyl)urea (compound 8)

Yield 58.3%, m.p. 224°–225° C.

EXAMPLE 9

N-[4-(2-Chlorophenyl)-2-phenylpyrimidin-5-yl]-N'-(2-methoxyphenyl)urea (compound 9)

Yield 79.1%, m.p. 241°–242° C.

EXAMPLE 10

N-[4-(2-Chlorophenyl)-2-phenylpyrimidin-5-yl]-N'-(2-methylthiophenyl)urea (compound 10)

Yield 64.5%, m.p. 196°–197° C.

EXAMPLE 11

N-[4-(2-Chlorophenyl)-2-phenylpyrimidin-5-yl]-N'-(2,4-dimethylphenyl)urea (compound 11)

Yield 82.3%, m.p. 212°–213° C.

EXAMPLE 12

N-[4-(2-Chlorophenyl)-2-phenylpyrimidin-5-yl]-N'-(3,4-dimethylphenyl)urea (compound 12)

Yield 81.6%, m.p. 216°–217° C.

EXAMPLE 13

N-[4-(2-Chlorophenyl)-2-phenylpyrimidin-5-yl]-N'-(2,6-dimethylphenyl)urea (compound 13)

Yield 66.0%, m.p. 241°–242° C.

EXAMPLE 14

N-[4-(2-Chlorophenyl)-2-phenylpyrimidin-5-yl]-N'-(2,6-diethylphenyl)urea (compound 14)

Yield 70.0%, m.p. 198°–199° C.

EXAMPLE 15

N-[4-(2-Chlorophenyl)-2-phenylpyrimidin-5-yl]-N'-(2,6-diisopropylphenyl)urea (compound 15)

Yield 76.5%, m.p. 200°–201° C.

EXAMPLE 16

N-[4-(2-chlorophenyl)-2-phenylpyrimidin-5-yl]-N'-(2-isopropyl-6-methylphenyl)urea (compound 16)

Yield 70.9%, m.p. 193°–194° C.

EXAMPLE 17

N-(2-t-Butyl-6-methylphenyl)-N'-[4-(2-chlorophenyl)-2-phenylpyrimidin-5-yl]urea (compound 17)

Yield 45.3%, m.p. 213°–216° C.

EXAMPLE 18

N-[4-(2-Chlorophenyl)-2-phenylpyrimidin-5-yl]N'-(2,4,6-trimethylphenyl) urea (compound 18)

Yield 35.0%, m.p. 225°–226° C.

EXAMPLE 19

N-[4-(2-Chlorophenyl)-2-phenylpyrimidin-5-yl]-N'-(2-dimethylamino-6-methylphenyl)urea (compound 19)

Yield 66.2%, m.p. 210°–211° C.

EXAMPLE 20

N-[4-(2-Chlorophenyl)-2-phenylpyrimidin-5-yl]-N'-(2-fluoro-4-methylphenyl)urea (compound 20)

Yield 35.2%, m.p. 206°–208° C.

EXAMPLE 21

N-[4-(2-Chlorophenyl)-2-phenylpyrimidin-5-yl]-N'-(2,4-difluorophenyl) urea (compound 21)

Yield 69.0%, m.p. 210°–211° C.

EXAMPLE 22

N-[4-(2-Chlorophenyl)-2-phenylpyrimidin-5-yl]-N'-(2,6-difluorophenyl)urea (compound 22)

Yield 45.6%, m.p. 202°–203° C.

EXAMPLE 23

N-[4-(2-Chlorophenyl)-2-phenylpyrimidin-5-yl]-N'-(2,4,6-trifluorophenyl)urea (compound 23)

Yield 73.7%, m.p. 230°–231° C.

EXAMPLE 24

N-[4-(2-Chlorophenyl)-2-phenylpyrimidin-5-yl]-N'-(2,6-dibromophenyl)urea (compound 24)

Yield 42.4%, m.p. 200°–202° C.

EXAMPLE 25

N-[4-(3-Chlorophenyl)-2-phenylpyrimidin-5-yl]-N'-(2,6-diethylphenyl)urea (compound 25)

Yield 64.9%, m.p. 275°–277° C.

EXAMPLE 26

N-[4-(3-Chlorophenyl)-2-phenylpyrimidin-5-yl]-N'-(2,6-diisopropylphenyl)urea (compound 26)

Yield 45.4%, m.p. 275°–276° C.

EXAMPLE 27

N-[4-(4-Chlorophenyl)-2-phenylpyrimidin-5-yl]-N'-(2,6-diethylphenyl)urea (compound 27)

Yield 69.0%, m.p. 285°–287° C.

EXAMPLE 28

N-[4-(4-Chlorophenyl)-2-phenylpyrimidin-5-yl]-N'-(2,6-diisopropylphenyl)urea (compound 28)

Yield 56.7%, m.p. >300° C.

EXAMPLE 29

N-[4-(2-(2,4-Dichlorophenyl)-2-phenylpyrimidin-5-yl]-N'-(2,6-diethylphenyl)urea (compound 29)

Yield 40.2%, m.p. 230°–232° C.

EXAMPLE 30

N-[4-(2,4-Dichlorophenyl)-2-phenylpyrimidin-5-yl]-N'-[2,6-diisopropylphenyl)urea (compound 30)

Yield 67.4%, m.p. 200°–201° C.

EXAMPLE 31

N-(2,6-Diethylphenyl)-N'-(2,4-diphenylpyrimidin-5-yl)urea (compound 31)

Yield 82.4%, m.p. 279°–280° C.

EXAMPLE 32

N-(2,6-Diisopropylphenyl)-N'-(2,4-diphenylpyrimidin-5-yl)urea (compound 32)

Yield 82.9%, m.p. 237°–238° C.

EXAMPLE 33

N-(2,6-Diethylphenyl)-N'-[4-(2-fluorophenyl)-2-phenylpyrimidin-5-yl]urea (compound 33)

Yield 60.1%, m.p. 219°–221° C.

EXAMPLE 34

N-(2,6-Diisopropylphenyl)-N'-[4-(2-fluorophenyl)-2-phenylpyrimidin-5-yl]urea (compound 34)

Yield 70.9%, m.p. 213°–214° C.

EXAMPLE 35

N-(2,6-Diethylphenyl)-N'-[4-(2-methylphenyl)-2-phenylpyrimidin-5-yl]urea (compound 35)

Yield 76.5%, m.p. 181°–182° C.

EXAMPLE 36

N-(2,6-Diisopropylphenyl)-N'-[4-(2-methylphenyl)-2-phenylpyrimidin-5-yl]urea (compound 36)

Yield 78.1%, m.p. 220°–222° C.

EXAMPLE 37

N-(2,6-Diethylphenyl)-N'-[2-phenyl-4-(2-trifluoromethylphenyl)pyrimidin-5-yl]urea (compound 37)

Yield 57.6%, m.p. 191°–192° C.

EXAMPLE 38

N-(2,6-Diisopropylphenyl)-N'-[2-phenyl-4-(2-trifluoromethylphenyl)pyrimidin-5-yl]urea (compound 38)

Yield 74.3%, m.p. 177°–179° C.

EXAMPLE 39

N-(2,6-Diethylphenyl)-N'-[4-(2-methoxyphenyl)-2-phenylpyrimidin-5-yl]urea (compound 39)

Yield 77.8%, m.p. 225°–226° C.

EXAMPLE 40

N-(2,6-Diisopropylphenyl)-N'-[4-(2-methoxyphenyl)-2-phenylpyrimidin-5-yl]urea (compound 40)

Yield 82.5%, m.p. 200°–201° C.

EXAMPLE 41

N-(2,6-Diethylphenyl)-N'-[4-(2-methylthiophenyl)-2-phenylpyrimidin-5-yl]urea (compound 41)

Yield 78.8%, m.p. 185°–187° C.

EXAMPLE 42

N-(2,6-Diisopropylphenyl)-N'-[4-(2-methylthiophenyl)-2-phenylpyrimidin-5-yl]urea (compound 42)

Yield 55.9%, m.p. 209°–210° C.

EXAMPLE 43

N-[4-(2-Chlorophenyl)-2-(3,5-dichlorophenyl)pyrimidin-5-yl]-N'-(2,6-diethylphenyl)urea (compound 43)

Yield 43.1%, m.p. 230°–231° C.

EXAMPLE 44

N-[4-(2-Chlorophenyl)-2-(3,5-dichlorophenyl)pyrimidin-5-yl]-N'-(2,6-diisopropylphenyl)urea (compound 44)

Yield 56.6%, m.p. 240°–241° C.

EXAMPLE 45

N-[4-(2-Chlorophenyl)-2-methylpyrimidin-5-yl]-N'-(2,6-diethylphenyl)urea (compound 45)

To a stirred mixture of 373 mg of 4-(2-chlorophenyl)-2-methyl-5-pyrimidinecarboxylic acid and 0.39 cc of diphenylphosphoryl azide in 5 cc of benzene was added dropwise 0.22 cc of triethylamine at room temperature. The resulting mixture was stirred at room temperature for 30 minutes and then heated under reflux for 30 minutes. After cooling, 0.3 cc of 2,6-diethylaniline was added, followed by refluxing for 3 hours. After cooling, water was added to the reaction mixture and extracted with chloroform. The extract was dried over magnesium sulfate, and distilled to remove the solvent. The crude product thus obtained was purified by a silica gel column chromatography (eluent: ethyl acetate/hexane=$\frac{3}{2}$) to obtain 510 mg of compound 45.

Yield 86.1%, m.p. 186°–187° C. NMR ($\delta$, ppm; DMSO-$d_6$) 1.08 (t, 6H), 2.47 (q, 4H), 2.59 (s, 3H), 7.11–7.23 (m, 3H), 7.50–7.60 (m, 3H), 7.66 (m, 1H), 7.85 (s, 1H), 8.01 (s, 1H), 9.11 (s, 1H).

The compounds described in Examples 46 to 50 were obtained in the same manner as in Example 45.

EXAMPLE 46

N-[4-(2-Chlorophenyl)-2-methylpyrimidin-5-yl]-N'-(2,6-diisopropylphenyl)urea (compound 46)

Yield 85.7%, m.p. 181°–182° C.

EXAMPLE 47

N-[4-(2-Chlorophenyl)-2-isopropylpyrimidin-5-yl]-N'-(2,6-diethylphenyl)urea (compound 47)

Yield 85.1%, m.p. 161°–162° C.

EXAMPLE 48

N-[4-(2-Chlorophenyl)-2-isopropylpyrimidin-5-yl]-N'-(2,6-diisopropylphenyl)urea (compound 48)

Yield 81.3%, m.p. 172°–174° C.

EXAMPLE 49

N-[2-t-Butyl-4-(2-chlorophenyl)pyrimidin-5-yl]-N'-(2,6-diethylphenyl)urea (compound 49)

Yield 88.5%, m.p. 209°–210° C.

EXAMPLE 50

N-[2-t-Butyl-4-(2-chlorophenyl)pyrimidin-5-yl]-N'-(2,6-diisopropylphenyl)urea (compound 50)

Yield 87.4%, m.p. 194° C.

EXAMPLE 51

N-[4-(2-Chlorophenyl)-2-ethoxypyrimidin-5-yl]-N'-(2,6-diethylphenyl)urea (compound 51)

To a stirred mixture of 418 mg of 4-(2-chlorophenyl)-2-ethoxy-5-pyrimidinecarboxylic acid and 0.39 cc of diphenylphosphoryl azide in 5 cc of benzene was added dropwise 0.22 cc of triethylamine at room temperature. The resulting mixture was stirred at room temperature for 30 minutes and then heated under reflux for 30 minutes. After cooling, 0.3 cc of 2,6-diethylaniline was added, followed by refluxing for 3 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform/methanol =$\frac{100}{1}$) to obtain 439 mg of compound 51.

Yield 68.9%, m.p. 190°–191° C. NMR ($\delta$, ppm; DMSO-$d_6$) 1.05 (t, 6H), 1.32 (t, 3H), 2.44 (q, 4H), 4.32 (q, 2H), 7.00–7.10 (m, 3H), 7.11–7.18 (m, 1H), 7.41–7.60 (m, 2H), 7.60–7.69 (m, 1H), 7.80 (s, 1H), 7.85 (s, 1H), 8.84 (s, 1H).

The compound described in Example 52 was obtained in the same manner as in Example 51.

EXAMPLE 52

N-[4-(2-Chlorophenyl)-2-ethoxypyrimidin-5-yl]-N'-(2,6-diisopropylphenyl)urea (compound 52)

Yield 67.7%, m.p. 141°–142° C.

EXAMPLE 53

N-[4-(2-Chlorophenyl)-2-(N-pyrrolidino)pyrimidin-5-yl]-N'-(2,6-diethylphenyl)urea (compound 53)

To a stirred mixture of 456 mg of 4-(2-chlorophenyl)-2-(N-pyrrolidino)-5-pyrimidinecarboxylic acid and 0.39 cc of diphenylphosphoryl azide in 6 cc of benzene was added dropwise 0.22 cc of triethylamine at room temperature. The resulting mixture was stirred at room temperature for 30 minutes and then heated under reflux for 20 minutes. After cooling, 0.3 cc of 2,6-diethylaniline was added, followed by refluxing for 3 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform/methanol=$\frac{100}{1}$) to obtain 588 mg of compound 53.

Yield 87.1%, m.p. 241°–242° C. NMR ($\delta$, ppm; DMSO-$d_6$) 1.03 (t, 6H), 1.92 (t, 4H), 2.38 (q, 4H), 3.46 (t, 4H), 7.00–7.08 (m, 2H), 7.08–7.10 (m, 1H), 7.40–7.62 (m, 6H), 8.43 (s, 1H).

The compounds described in Examples 54 to 60 were obtained in the same manner as in Example 53.

EXAMPLE 54

N-[4-(2-Chlorophenyl)-2-(N-pyrrolidino)pyrimidin-5-yl]-N'-(2,6-diisopropylphenyl)urea (compound 54)

Yield 88.6%, m.p. 224°–225° C.

EXAMPLE 55

N-[4-(2-Chlorophenyl)-2-(N-piperidino)pyrimidin-5-yl]-N'-(2,6-diethylphenyl)urea (compound 55)

Yield 79.3%, m.p. 235°–238° C.

EXAMPLE 56

N-[4-(2-Chlorophenyl)-2-(N-piperidino)pyrimidin-5-yl]-N'-(2,6-diisopropylphenyl)urea (compound 56)

Yield 84.0%, m.p. 222°–224° C.

EXAMPLE 57

N-[4-(2-Chlorophenyl)-2-(N-morpholino)pyrimidin-5-yl]-N'-(2,6-diethylphenyl)urea (compound 57)

Yield 88.3%, m.p. 255°–256° C.

EXAMPLE 58

N-[4-(2-Chlorophenyl)-2-(N-morpholino)pyrimidin-5-yl]-N'-(2,6-diisopropylphenyl)urea (compound 58)

Yield 85.6%, m.p. 224°–225° C.

EXAMPLE 59

N-[4-(2-Chlorophenyl)-2-(4-methyl-1-piperazino)pyrimidin-5-yl]-N'-(2,6-diethylphenyl)urea (compound 59)

Yield 65.1%, m.p. 210°–212° C.

EXAMPLE 60

N-[4-(2-Chlorophenyl)-2-(4-methyl-1-piperazino)pyrimidin-5-yl]-N'-(2,6-diisopropylphenyl)urea (compound 60)

Yield 70.5%, m.p. 212°–214° C.

EXAMPLE 61

N-(2,6-Diisopropylphenyl)-N'-(2,6-diphenylpyridin-3-yl)urea (compound 61)

To a stirred mixture of 551 mg of 2,6-diphenyl-3-pyridinecarboxylic acid and 0.52 cc of diphenylphosphoryl azide in 6 cc of fluorobenzene was added dropwise 0.29 cc of triethylamine at room temperature. The resulting mixture was stirred at room temperature for 30 minutes and then heated at a temperature of 65°–70° C. for 10 minutes. After cooling, 0.45 cc of 2,6-diisopropylaniline was added and the resulting mixture was heated at a temperature of 70° C. for 1.5 hours. After cooling, water was added to the reaction mixture and extracted with chloroform. The extract was dried over magnesium sulfate, and distilled to remove the solvent. The crude product thus obtained was purified by a silica gel column chromatography (eluent: chloroform) to obtain 817 mg of compound 61.

Yield 90.9%, m.p. 206°–208° C. NMR (δ, ppm; DMSO-$d_6$) 1.16 (d, 12H), 3.16 (m, 2H), 7.05–7.19 (m, 3H), 7.20–7.26 (m, 1H), 7.35–7.60 (m, 5H), 7.76–7.78 (m, 2H), 7.92–7.94 (m, 1H), 8.05

8.13(m, 3H), 8.15 (s, 1H), 8.20–8.23 (m, 1H).

The compounds described in Examples 62 to 67 were obtained in the same manner as in Example 61.

EXAMPLE 62

N-[2-(2-Chlorophenyl)-6-phenylpyridin-3-yl]-N'-(2,6-diethylphenyl)urea (compound 62)

Yield 69.7%, m.p. 190°–191° C.

EXAMPLE 63

N-[2-(2-Chlorophenyl)-6-phenylpyridin-3-yl]-N'-(2,6-diisopropylphenyl)urea (compound 63)

Yield 79.9%, m.p. 241°–242° C.

EXAMPLE 64

N-[2-(2-Chlorophenyl)-6-methylpyridin-3-yl]-N'-(2,6-diisopropylphenyl)urea (compound 64)

Yield 92.0%, amorphous. NMR (δ, ppm; DMSO-$d_6$) 1.12 (d, 12H), 2.42 (s, 3H), 3.08 (m, 2H), 7.10–7.12 (m, 2H), 7.19–7.24 (m, 2H), 7.43–7.61 (m, 5H), 7.94 (s, 1H), 8.10–8.12 (m, 1H).

EXAMPLE 65

N-[2-(2-Chlorophenyl)-6-(n-heptyl)pyridin-3-yl]-N'-(2,6-diisopropylphenyl)urea (compound 65)

Yield 92.2%, m.p. 74°–75° C.

EXAMPLE 66

N-[2-(2-Chlorophenyl)-6-cyclohexylpyridin-3-yl]-N'-(2,6-diethylphenyl)urea (compound 66)

Yield 74.7%, m.p. 122°–124° C.

EXAMPLE 67

N-[2-(2-Chlorophenyl)-6-cyclohexylpyridin-3-yl]-N'-(2,6-diisopropylphenyl)urea (compound 67)

Yield 83.8%, m.p. 202°–203° C.

REFERENCE EXAMPLE 1

4-(2-Chlorophenyl)-6-methyl-2-phenyl-5-pyrimidinecarboxylic acid

1) Ethyl 2-(2-chlorobenzylidene)acetoacetate (compound A)

A mixture of 25.0 g of 2-chlorobenzaldehyde, 23.1 g of ethyl acetoacetate, 2.1 g of acetic acid and 0.6 g of piperidine in 100 cc of benzene was heated under reflux for 8 hours and removed water by a Dean-Stark trap. After cooling, to the reaction mixture was added ethylacetate and water. The organic layer was further washed with a saturated aqueous sodium chloride solution and dried over magnesium sulfate.

The solvent was distilled off and the crude product thus obtained was purified by a silica gel column chromatography (eluent: ethyl acetate/hexane=⅛) to obtain 44.0 g of compound A. Yield: 97.9%.

2) Ethyl 1,6-dihydro-6-(2-chlorophenyl)-4-methyl-2-phenyl-5-carboxylate (compound B)

A mixture of 2.53 g of compound A, 1.88 g of benzamidine hydrochloride and 2.73 g of triethylamine in 20 cc of n-butanol was heated under reflux for 90 minutes. After cooling, to the reaction mixture was added ethyl acetate and water. The organic layer was further washed two times with water and dried over magnesium sulfate. The solvent was distilled off and the crude product thus obtained was purified by a silica gel column chromatography (eluent: ethyl acetate/hexane =⅓) to obtain 2.71 g of compound B. Yield: 76.4%.

3) Ethyl 4-(2-chlorophenyl)-2-phenyl-6-methyl-5-pyrimidinecarboxylate (compound C)

To a stirred solution of 2.71 g of compound B in 50 cc of toluene was added 2.08 g of 2,3-dichloro- 5,6-dicyano-1,4-benzoquinone at room temperature and the resulting mixture was heated at a temperature of 40°–50° C. for 1 hour. After cooling, the toluene was distilled off and a cyclohexane-AcOEt (4/1) solution was added to the residue. The insoluble material was filtered off and further washed with a cyclohexane-AcOEt (4/1) solution. The combined filtrate was distilled to remove the solvent. The crude product thus obtained was purified by a silica gel column chromatography (eluent: ethyl acetate/hexane=⅛) to obtain 2.0 g of compound C. Yield: 74.2%.

4) 4-(2-Chlorophenyl)-2-phenyl-6-methyl-5-pyrimidine-carboxylic acid

A mixture of 3.0 g of compound C and 1.43 g of powdered KOH in 20 cc ethanol was heated under reflux for 2 hours. After cooling, the reaction mixture was acidified with 1N HCl, and extracted with chloroform. The extract was dried over magnesium sulfate, and distilled to remove the solvent. Thus, 2.75 g of 4-(2-chlorophenyl)- 2-phenyl-6-methyl-5-pyrimidinecarboxylic acid was obtained. Yield: 99.6%.

REFERENCE EXAMPLE 2

4-(2-Chlorophenyl)-2-phenyl-5-pyrimidinecarboxylic acid

1) Ethyl 2-(2-chlorobenzoyl)-3-dimethylaminopropenoate (compound D)

To a stirred solution of 5.0 g of ethyl 2-chlorobenzoylacetate in 50 cc of benzene was added dropwise 5 cc of dimethylformamide dimethylacetal in 15 cc of benzene at room temperature. The resulting mixture was heated under reflux for 6 hours. After cooling, the solvent was distilled off to obtain 6.2 g of compound D. Yield: 97.3%.

2) Ethyl 4-(2-chlorophenyl)-2-phenyl-5-pyrimidinecarboxylate (compound E)

To a stirred solution of 3.45 g of benzamidine hydrochloride in 50 cc of ethanol was added 1.50 g of sodium ethoxide at room temperature and the mixture was stirred for 10 minutes. The resulting suspension was added to 6.2 g of compound D in 50 cc of ethanol and the resulting mixture was heated under reflux for 6 hours. After cooling, the solvent was distilled off, and AcOEt and water were added to the residue. The organic layer was further washed with a saturated aqueous sodium bicarbonate solution and dried over magnesium sulfate. The solvent was distilled off and the crude product thus obtained was purified by a silica gel column chromatography (eluent: ethyl acetate/hexane=⅛) to obtain 5.80 g of compound E. Yield: 77.6%.

3) 4-(2-Chlorophenyl)-2-phenyl-5-pyrimidinecarboxylic acid

A mixture of 5.70 g of compound E and 2.83 g of potassium hydroxide in 40 cc of ethanol and 0.5 cc of water was heated under reflux for 3 hours. After cooling, the reaction mixture was acidified with 1N HCl, and extracted with chloroform. The extract was dried over magnesium sulfate, and distilled to remove the solvent. Thus, 5.20 g of 4-(2-chlorophenyl)-2-phenyl-5-pyrimidinecarboxylic acid was obtained. Yield: 99.6%.

The following compounds were obtained in the same manner as in Reference Example 2:

(1) 4-(3-chlorophenyl)-2-phenyl-5-pyrimidinecarboxylic acid, (2) 4-(4-chlorophenyl)-2-phenyl-5-pyrimidinecarboxylic acid, (3) 4-(2,4-dichlorophenyl)-2-phenyl-5-( pyrimidinecarboxylic acid, (4) 2,4-diphenyl-5-pyrimidinecarboxylic acid, (5) 4-(2-fluorophenyl)-2-phenyl-5-pyrimidinecarboxylic acid, (6) 4-(2-methylphenyl)-2-phenyl-5-pyrimidinecarboxylic acid, (7) 2-phenyl-4-(2-trifluoromethylphenyl)-5-pyrimidinecarboxylic acid, (8) 4-(2-methoxylphenyl)-2-phenyl-5-pyrimidinecarboxylic acid, (9) 4-(2-methylthiophenyl)-2-phenyl-5-pyrimidinecarboxylic acid,

(10) 4-(2-chlorophenyl)-2-(3,5-dichlorophenyl)-5-pyrimidinecarboxylic acid.

REFERENCE EXAMPLE 3

4-(2-Chlorophenyl)-2-methyl-5-pyrimidinecarboxylic acid

1) Ethyl 4-(2-chlorophenyl)-2-methyl-5-pyrimidinecarboxylate (compound F)

To a stirred solution of 2.09 g of acetoamidine hydrochloride in 50 cc of ethanol was added 1.50 g of sodium ethoxide at room temperature and the mixture was stirred for 10 minutes. The resulting suspension was added to 6.1 g of compound D in 50 cc of ethanol and the resulting mixture was heated under reflux for 6 hours. Thereafter, 4.5 g of compound F was obtained in the same manner as for compound E. Yield: 73.7%.

2) 4-(2-Chlorophenyl)-2-methyl-5-pyrimidinecarboxylic acid

In the same manner as in the production of 4-(2-chlorophenyl)-2-phenyl-5-pyrimidinecarboxylic acid from compound E, 3.7 g of 4-(2-chlorophenyl)-2-methyl-5-pyrimidinecarboxylic acid was obtained from 4.5 g of compound F. Yield: 91.3%.

The following compounds were obtained in the same manner as in Reference Example 3:
(1) 4-(2-chlorophenyl)-2-isopropyl-5-pyrimidinecarboxylic acid,
(2) 2-t-butyl-4-(2-chlorophenyl)-5-pyrimidinecarboxylic acid,
(3) 4-(2-chlorophenyl)-2-ethoxy-5-pyrimidinecarboxylic acid,
(4) 4-(2-chlorophenyl)-2-(N-pyrrolidino)-5-pyrimidinecarboxylic acid,
(5) 4-(2-chlorophenyl)-2-(N-piperidino)-5-pyrimidinecarboxylic acid,
(6) 4-(2-chlorophenyl)-2-(N-morpholino)-5-pyrimidinecarboxylic acid,
(7) 4-(2-chlorophenyl)-2-(4-methyl-1-piperazino)-5-pyrimidinecarboxylic acid.

REFERENCE EXAMPLE 4

2,6-Diphenyl-3-pyridinecarboxylic acid

1) Ethyl 2-benzoyl-5-oxo-5-phenylvalerate (compound G)

To a stirred mixture of 2.14 g of β-dimethylaminopropiophenone hydrochloride and 1.92 g of ethyl benzoylacetate in 30 cc of ethanol was added in small portions 1.36 g of sodium ethoxide at room temperature. The resulting mixture was stirred at room temperature for 30 minutes and then heated under reflux for 1 hour. After cooling, the solvent was distilled off and water was added to the residue. The aqueous layer was acidified with 1N HCl, and extracted twice with chloroform. The combined organic layer was washed with a saturated aqueous sodium chloride solution and dried over magnesium sulfate. The solvent was distilled off and the crude product thus obtained was purified by a silica gel column chromatography (eluent: ethyl acetate/hexane=1/5) to obtain 2.45 g of compound G. Yield: 75.5%.

2) Ethyl 2,6-diphenyl-3-pyridinecarboxylate (compound H)

A mixture of 2.30 g of compound G, 8.20 g of ammonium acetate and 8.43 g of ferric chloride hexahydrate in 50 cc of acetic acid was heated under reflux for 7 hours. After cooling, the insoluble materials were removed by filtration through Celite and the filtrate was distilled to remove the solvent. The residue was adjusted to pH 8 with an aqueous sodium bicarbonate solution, and extracted three times with ethyl acetate. The combined organic layer was washed with a saturated aqueous sodium chloride solution and dried over magnesium sulfate. The solvent was distilled off and the crude product thus obtained was purified by a silica gel column chromatography (eluent: ethyl acetate/hexane=1/5) to obtain 1.98 g of compound H. Yield: 92.1%.

3) 2,6-Diphenyl-3-pyridinecarboxylic acid

In the same manner as in the production of 4-(2-chlorophenyl)-2-phenyl-5-pyrimidinecarboxylic acid from compound E, 1.62 g of 2,6-diphenyl-3-pyridinecarboxylic acid was obtained from 1.90 g of compound H. Yield: 95.0%.

The following compound was obtained in the same manner as in Reference Example 4:
2-(2-chlorophenyl)-6-phenyl-3-pyridinecarboxylic acid.

REFERENCE EXAMPLE 5

2-(2-Chlorophenyl)-6-n-heptyl-3-pyridinecarboxylic acid

1) Ethyl 5-oxo-2-(2-chlorobenzoyl)laurate (compound I)

To a stirred solution of 0.91 g of ethyl 2-chlorobenzoylacetate in 10 cc of ethanol was added 0.27 g of sodium ethoxide at room temperature, and the mixture was stirred at room temperature for 10 minutes. Then, 0.62 g of 3-oxo-1-decene in 10 cc of ethanol was added and the resulting mixture was stirred overnight at room temperature. Water was added to the reaction mixture, and the aqueous layer was acidified with 1N HCl and extracted three times with ethyl acetate. The combined organic layer was washed with a saturated aqueous sodium chloride solution and dried over magnesium sulfate. The solvent was distilled off and the crude product thus obtained was purified by a silica gel column chromatography (eluent: ethyl acetate/hexane =1/5) to obtain 0.90 g of compound I. Yield: 59.1%.

2) 2-(2-Chlorophenyl)-6-n-heptyl-3-pyridinecarboxylic acid (compound J)

A mixture of 0.90 g of compound I, 2.73 g of ammonium acetate and 2.80 g of ferric chloride hexahydrate in 20 cc of acetic acid was heated under reflux for 8 hours. Thereafter, 0.60 g of compound J was obtained in the same manner as in the production of compound H from compound G, Yield: 70.6%.

3) 2-(2-Chlorophenyl)-6-n-heptyl-3-pyridinecarboxylic acid

In the same manner as in the production of 4-(2-chlorophenyl)-2-phenyl-5-pyrimidinecarboxylic acid from compound E, 0.47 g of 2-(2-chlorophenyl)-6-n-heptyl-3-pyridinecarboxylic acid was obtained from 0.60 g of compound J. Yield: 85.0%.

The following compounds were obtained in the same manner as in Reference Example 5:
(1) 2-(2-chlorophenyl)-6-methyl-3-pyridinecarboxylic acid,
(2) 2-(2-chlorophenyl)-6-cyclohexyl-3-pyridinecarboxylic acid.

In the following formulation examples, parts are all by weight.

FORMULATION EXAMPLE 1

A powder was prepared by mixing uniformly and pulverizing or granulating finely the following ingredients:

| Each compound of the invention | 10 parts |
|---|---|
| Magnesium stearate | 10 parts |
| Lactose | 80 parts |

FORMULATION EXAMPLE 2

Granules were prepared by kneading together uniformly, grinding, and granulating the following ingredients, followed by sieving:

| Each compound of the invention | 50 parts |
|---|---|
| Starch | 10 parts |
| Lactose | 15 parts |
| Ethyl cellulose | 20 parts |
| Poly(vinyl alcohol) | 5 parts |
| Water | 30 parts |

FORMULATION EXAMPLE 3

Tablets with a diameter of 10 mm were prepared by mixing 99 parts of the granules obtained in Formulation Example 2 with 1 part of calcium stearate, and compression-molding the resulting mixture.

FORMULATION EXAMPLE 4

Granules were prepared in the same manner as in Formulation Example 2 except for using the following ingredients:

| Each compound of the invention | 95 parts |
|---|---|
| Poly(vinyl alcohol) | 5 parts |
| Water | 30 parts |

To 90 parts of the granules obtained was added 10 parts of crystalline cellulose, and the resulting mixture was compression-molded into tablets with a diameter of 8 mm. Then, the tablets were made into dragee by the use of suitable amounts of a mixed suspension of syrup, gelatin and precipitated calcium carbonate and a coloring agent.

FORMULATION EXAMPLE 5

An injection was prepared by mixing by heating, and then sterilizing the following ingredients:

| Each compound of the invention | 0.5 parts |
|---|---|
| Nonionic surfactant | 2.5 parts |
| Physiological saline | 97 parts |

FORMULATION EXAMPLE 6

Capsules were prepared by packing the powder obtained in Formulation Example 1 into commercially available capsular containers.

Next, test examples are described below for proving the effectiveness of the present invention.

TEST EXAMPLE 1

Inhibitory activity on acyl-CoA:cholesterol acyltransferase (ACAT)

The enzyme used in the test was prepared according to the method of Heider et al. [J. Lipid, Res. 24, 1127 (1983)]. The intestinal mucosa of a white rabbit was homogenized and microsomal fraction was obtained by stepwise centrifugation. The microsomal fraction was suspended in 0.154M phosphate buffer (pH 7.4) and stored at $-80°$ C. until use.

ACAT activity was determined by a modification of the method of Helgerud et al. [J. Lipid Res. 22, 271 (1981)] by measuring radioactivity incorporated into cholesterol esters from $[1-{}^{14}C]$oleyl-CoA, as an indication. As to the ACAT-inhibitory activity of each compound to be tested, the inhibition rate was calculated by the following equation. The results obtained are shown in Table 2.

Inhibition rate (%) =

$$\frac{\left[\begin{array}{c}ACAT \text{ activity}\\ \text{of control}\\ \text{group which}\\ \text{was given}\\ \text{solvent}\end{array}\right] - \left[\begin{array}{c}ACAT \text{ activity}\\ \text{of group}\\ \text{treated with}\\ \text{compound to}\\ \text{be tested}\end{array}\right]}{\left[\begin{array}{c}ACAT \text{ activity of control}\\ \text{group which was given}\\ \text{solvent}\end{array}\right]} \times 100$$

TABLE 2

| Compound No. | [Inhibition rate %] 1 | 0.01 µM | Compound No. | [Inhibition rate %] 1 | 0.01 µM |
|---|---|---|---|---|---|
| 1 | 98.0 | 16.7 | 37 | | 72.3 |
| 2 | 99.2 | 58.5 | 40 | | 47.5 |
| 3 | 88.3 | | 41 | | 56.3 |
| 6 | 23.0 | | 44 | | 46.8 |
| 13 | 97.5 | 40.2 | 46 | | 32.0 |
| 14 | 99.0 | 58.8 | 50 | | 48.4 |
| 15 | 99.5 | 67.6 | 52 | | 64.7 |
| 18 | 79.7 | | 53 | | 70.0 |
| 19 | | 35.9 | 55 | | 75.7 |
| 23 | 87.0 | | 56 | | 69.5 |
| 26 | | 58.9 | 57 | | 63.2 |
| 28 | | 40.7 | 60 | | 40.1 |
| 30 | | 37.1 | 63 | | 53.1 |
| 32 | | 73.5 | 64 | | 43.6 |
| 34 | | 65.8 | 65 | | 29.8 |
| 36 | | 72.9 | 67 | | 58.0 |

TEST EXAMPLE 2

Serum cholesterol lowering activity in hamsters fed on a high-cholesterol diet

Male Syrian hamsters of 10-week-old were divided into three groups. The first group (normal group) was fed an ordinary diet for 4 days. The second group (control group) was fed a high cholesterol diet (containing 0.5% cholesterol and 8.0% coconut oil) for 4 days. The third group (treated group) was fed a high cholesterol diet and was treated with a compound for 4 days. Simultaneously with the beginning of the above feeding, the compound was suspended in a 0.5% carboxymethyl cellulose solution and administered to the treated group, in a dose of 30 mg (in terms of the compound) per kg of body weight per day for 4 days. A 0.5% carboxymethyl cellulose solution was also administered to the normal group and the control group in the same manner as above.

After 24 hours of the last administration, blood was collected and the cholesterol concentration in serum was measured by an enzymatic method. The reduction rate of the total serum cholesterol concentration was calculated from values obtained for the three groups by the following equation. The results obtained are shown in Table 3.

$$\text{cholesterol reduction rate (\%)} = \frac{(A) - (B)}{(A) - (c)} \times 100$$

wherein

A: the serum cholesterol concentration of the control group.

B: the serum cholesterol concentration of the treated group.

C: the serum cholesterol concentration of the normal group.

TABLE 3

| Compound No. | Reduction rate (%) |
| --- | --- |
| 2 | 42.7 |
| 14 | 59.4 |
| 15 | 57.6 |
| 32 | 63.7 |
| 34 | 74.0 |
| 36 | 63.4 |
| 37 | 63.3 |
| 55 | 77.5 |
| 57 | 59.5 |

TEST EXAMPLE 3

Inhibitory effect on cholesterol esterification in macrophages

The test was carried out by a modification of the method of Goldstein et al. [Pro. Nat. Acad. Sci. U.S.A. 71, 4288 (1974)]. J774 A.I cells, the mouse macrophage-like cell line, were suspended in Dulbecco's modified Eagle's medium (DMEM) containing 10% fetal calf serum (FCS), in a proportion of $3 \times 10^5$ cells per 2 ml and were seeded into 6-well plates. The cells were cultured under a humidified atmosphere of 95% air/5% $CO_2$ at 37° C. for 24 hours. The medium was replaced by 1 ml of DMEM containing 10% of FCS and 50 μg/ml of acetylated human low density lipoprotein (AcLDL), followed by culturing for 16 hours. Five microliters of each compound dissolved in dimethyl sulfoxide was added to the medium, and the cells were cultured for another 2 hours. Then, [$^{14}C$]oleate ($2 \times 10^6$ dpm/well) bovine serum albumin complex was added in the medium. After 2 hours of culture, cells were collected and the cholesterol-esterifying activity was determined by measuring radioactivity incorporated into cholesterol esters in the cells. The recovery of the cholesterol esters was determined by the addition of [$^3H$]cholesteryl oleate, and the esterifying activity was corrected using the recovery. As to the inhibitory activity on cholesterol esterification of the compound to be tested, the inhibition rate was calculated by the following equation. The results obtained are shown in Table 4.

$$\text{Inhibition rate of cholesterol esterification (\%)} = \frac{(B) - (A)}{(B)} \times 100$$

wherein

A: the cholesterol-esterifying activity of AcLDL-loaded cells to which the compound to be tested was added.

B: the cholesterol-esterifying activity of AcLDL-loaded cells to which dimethyl sulfoxide was added.

TABLE 4

| | (Inhibition rate %) | |
| --- | --- | --- |
| Compound No. | 1 | 0.3 μM |
| 15 | 73.3 | 29.5 |
| 32 | 74.3 | 58.0 |
| 36 |  | 51.6 |
| 37 | 87.2 | 67.1 |
| 55 |  | 34.9 |

The compounds of the present invention have ACAT-inhibitory activity and are useful as a prophylactic and therapeutic agent for hypercholesterolemia, atherosclerosis and various diseases caused by them.

What is claimed is:

1. A pyrimidine or pyridine derivative represented by the formula (I):

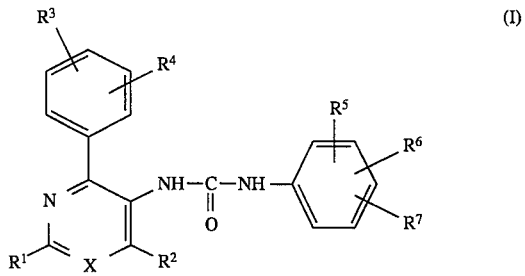

wherein $R^1$ is a lower alkyl group, a lower cycloalkyl group, a lower alkoxy group, an aliphatic cyclic amino group which may be substituted by one or more lower alkyl groups, the said aliphatic cyclic amino group is selected from the group consisting of pyrrolidino, piperidino, and the group represented by the formula

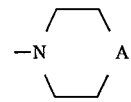

wherein A represents —O—, —S—, —N(R)— in which R represents hydrogen atom or a lower alkyl group, or a phenyl group which may be substituted by one or more halogen atoms provided that $R^1$ is a group other than said aliphatic cyclic amino group when X is =CH—, $R^2$ is a hydrogen atom or a lower alkyl group, $R^3$ and $R^4$, which may be the same or different, are hydrogen atoms, halogen atoms, lower alkyl groups, lower haloalkyl groups, lower alkoxy groups or lower alkylthio groups, $R^5$, $R^6$ and $R^7$, which may be the same or different, are hydrogen atoms, halogen atoms, lower alkyl groups, lower haloalkyl groups, lower alkoxy groups, lower alkylthio groups or lower dialkylamino groups, and X is =N— or =CH—; or a pharmaceutically acceptable salt thereof.

2. A pyrimidine or pyridine derivative or a pharmaceutically acceptable salt thereof according to claim 1, wherein $R^1$ is a lower alkyl group, a lower cycloalkyl group, a lower alkoxy group, an aliphatic cyclic amino group which may be substituted by one or more lower alkyl groups, or a phenyl group, $R^2$ is a hydrogen atom or a lower alkyl group, $R^3$ is a hydrogen atom, a halogen atom, a lower alkyl group, a lower haloalkyl group, a lower alkoxy group or a lower alkylthio group, $R^4$ is a hydrogen atom, $R^5$ and $R^6$ are independently a lower alkyl group, and $R^7$ is a hydrogen atom.

3. A pyrimidine or pyridine derivative or a pharmaceutically acceptable salt thereof according to claim 1, wherein $R^1$ is a cyclohexyl group, a piperidino group, a morpholino group or a phenyl group, $R^2$ is a hydrogen atom or a lower alkyl group, $R^3$ is a fluorine atom, a chlorine atom, a lower alkyl group, a lower haloalkyl group or a lower alkylthio group, $R^4$ is a hydrogen atom, and $R^5$ and $R^6$ are independently a lower alkyl group.

4. An ACAT inhibitor comprising as an active ingredient a pyrimidine or pyridine derivative represented by the formula (I):

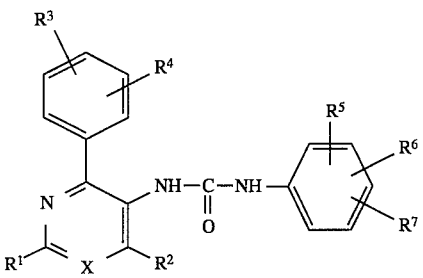

(I)

wherein $R^1$ is a lower alkyl group, a lower cycloalkyl group, a lower alkoxy group, an aliphatic cyclic amino group which may be substituted by one or more lower alkyl groups, the said aliphatic cyclic amino group is selected from the group consisting of pyrrolidino, piperidino, and the groups represented by the formula

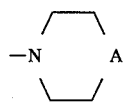

wherein A represents —O—, —S—, —N(R)— in which R represents hydrogen atom or a lower alkyl group, or a phenyl group which may be substituted by one or more halogen atoms provided that $R^1$ is a group other than said aliphatic cyclic amino group when X is =CH—, $R^2$ is a hydrogen atom or a lower alkyl group, $R^3$ and $R^4$, which may be the same or different, are hydrogen atoms, halogen atoms, lower alkyl groups, lower haloalkyl groups, lower alkoxy groups or lower alkylthio groups, $R^5$, $R^6$ and $R^7$, which may be the same or different, are hydrogen atoms, halogen atoms, lower alkyl groups, lower haloalkyl groups, lower alkoxy groups, lower alkylthio groups or lower dialkylamino groups, and X is =N— or =CH—; or a pharmaceutically acceptable salt thereof; and pharmaceutically acceptable carriers.

5. An ACAT inhibitor according to claim 4, wherein $R^1$ is a lower alkyl group, a lower cycloalkyl group, a lower alkoxy group, an aliphatic cyclic amino group which may be substituted by one or more lower alkyl groups, or a phenyl group, $R^2$ is a hydrogen atom or a lower alkyl group, $R^3$ is a hydrogen atom, a halogen atom, a lower alkyl group, a lower haloalkyl group, a lower alkoxy group or a lower alkylthio group, $R^4$ is a hydrogen atom, $R^5$ and $R^6$ are independently a lower alkyl group, and $R^7$ is a hydrogen atom.

6. An ACAT inhibitor according to claim 4 wherein $R^1$ is a cyclohexyl group, a piperidino group, a morpholino group or a phenyl group, $R^2$ is a hydrogen atom or a lower alkyl group, $R^3$ is a fluorine atom, a chlorine atom, a lower alkyl group, a lower haloalkyl group or a lower alkylthio group, $R^4$ is a hydrogen atom, and $R^5$ and $R^6$ are independently a lower alkyl group.

* * * * *